United States Patent
Kinno et al.

(10) Patent No.: US 6,862,338 B2
(45) Date of Patent: Mar. 1, 2005

(54) IMAGING DEVICE (75) Inventors: Akira Kinno, Kanagawa-Ken (JP); Mitsushi Ikeda, Kanagawa-Ken (JP)

(73) Assignee: Kabushiki Kaisha Toshiba, Tokyo (JP)

(*) Notice: Subject to any disclaimer, the term of this patent is extended or adjusted under 35 U.S.C. 154(b) by 24 days.

(21) Appl. No.: 10/436,235

(22) Filed: May 13, 2003

(65) Prior Publication Data
US 2003/0215058 A1 Nov. 20, 2003

(30) Foreign Application Priority Data
May 14, 2002 (JP) ........................................ 2002-138921

(51) Int. Cl.[7] .............................................. H05G 1/64
(52) U.S. Cl. .................... 378/98.8; 378/19; 250/370.09
(58) Field of Search ............................ 378/98.8, 19, 9, 378/97; 250/370.09

(56) References Cited

U.S. PATENT DOCUMENTS

| | | | |
|---|---|---|---|
| 4,689,487 A | | 8/1987 | Nishiki et al. |
| 6,225,632 B1 | * | 5/2001 | Kinno et al. ............ 250/370.09 |
| 6,353,229 B1 | | 3/2002 | Polischuk et al. |
| 6,724,855 B2 | * | 4/2004 | Sugawara et al. ............. 378/19 |
| 6,751,289 B2 | * | 6/2004 | Aoki et al. ................. 378/98.7 |
| 6,760,405 B2 | * | 7/2004 | Ruetten et al. ............ 378/98.8 |

FOREIGN PATENT DOCUMENTS

JP    2002-58804    2/2000

* cited by examiner

Primary Examiner—David V. Bruce
Assistant Examiner—Irakli Kiknadze
(74) Attorney, Agent, or Firm—Finnegan, Henderson, Farabow, Garrett & Dunner, L.L.P.

(57) ABSTRACT

There are provided a photoelectric conversion film converting an x-ray to a charge, a switching element composed of a transistor, of which a gate is connected to a corresponding scanning line, a source is connected to the photoelectric conversion film, and a drain is connected to a corresponding signal line, and a accumulation element connected to the photoelectric conversion film and the switching element, accumulating the charged produced in the photoelectric conversion element, a scanning line driving circuit driving the scanning lines, and a signal detection circuit connected to the signal lines and reading out the charge accumulated in the accumulation element. A potential of the photoelectric conversion film and a gate potential of the switching element is set such that an absolute value of a gate-source voltage of the switching element decreases when the charge is accumulated in the accumulation element. The scanning line driving circuit outputs at least two kinds of scanning line voltages that can turn off the switching element.

14 Claims, 11 Drawing Sheets

IMAGING DEVICE

CROSS-REFERENCE TO RELATED APPLICATIONS

This application is based upon and claims the benefit of priority from the prior Japanese Patent Application No. 2002-138921, filed on May 14, 2002 in Japan, the entire contents of which are incorporated by reference.

BACKGROUND OF THE INVENTION

1. Field of the Invention

The present invention relates to imaging devices for converting optical signals to electric signals, and more particularly, to an x-ray CT (computerized tomography) imaging device system for medical applications.

2. Related Art

Recently, x-ray imaging device systems have been proposed as a possible application of TFT (thin-film transistor) arrays (for example, see U.S. Pat. No. 4,689,487). X-ray CT systems are also considered as a possible application of TFT arrays.

Figure 8:
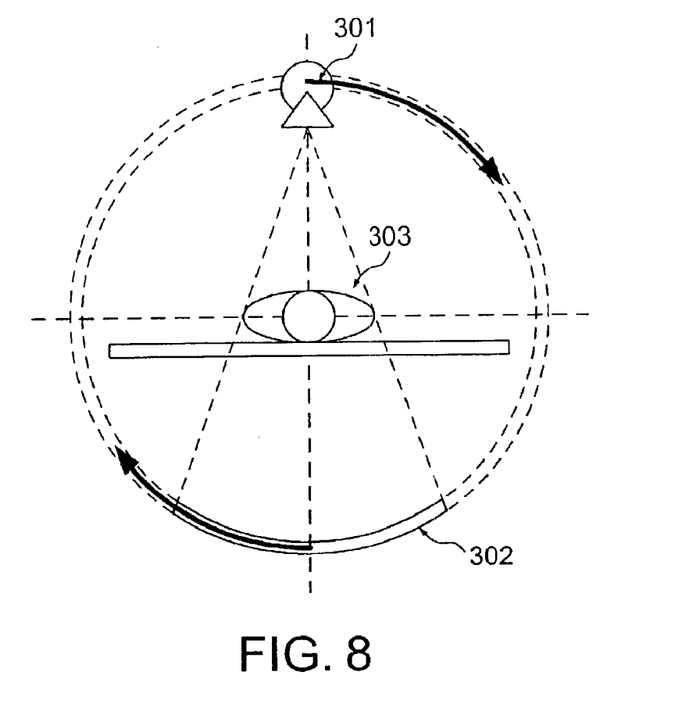
FIG. 8 schematically shows an x-ray CT system.

As shown in FIG. 8, an x-ray CT system has a structure that an x-ray source 301 and a detector 302 are located on opposite sides relative to an object person 303. The detector 302 is composed of a scintillation detector for converting an x-ray to an optical signal, and a photodiode for converting an optical signal to an electric signal. An x-ray emitted from the x-ray source 301 passes through the object person 303 to reach the detector 302. The detector 302 outputs an electric signal corresponding to the intensity of the x-ray, thereby forming an image.

In a helical scan type x-ray CT system, the x-ray source 301 and the detector 302 helically rotates in the direction of the body axis of the object person 303, and thereby sequentially collects x-ray images. While the detector 302 collects about 2,000 x-ray images per second, the x-ray source 301 keeps emitting x-ray. A sectional view of the object person 303 is formed by combining the x-ray images collected by the detector 302.

Figure 9:
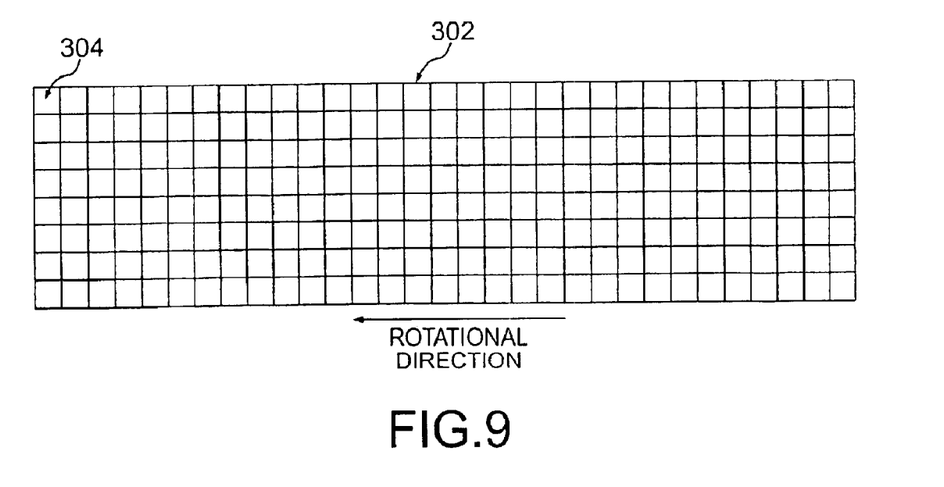
FIG. 9 shows the structure of a multi-slice type detector.

In recent x-ray CT systems, multi-slice type detectors are employed in order to shorten the imaging time. FIG. 9 shows a multi-slice type detector 302. A detecting element 304 provided to each horizontally extending line collects one slice of x-ray image. In FIG. 9, eight detecting elements 304 are provided so as to collect eight slices of an image at a time. Since the imaging time can be shortened, the time during which the object-person must be still can be shortened, thereby decreasing the total x-ray dose.

A detector using a TFT array is proposed to replace the detectors now on the market. With such a detector, it is possible to easily increase the number of slices, thereby easily shortening the imaging time and decreasing the x-ray dose. Further, it is possible to reduce the pixel size, thereby obtaining high-definition images.

In order to obtain a high-definition image, it is important to employ an x-ray-to-charge conversion method, which is called the direct conversion method, in addition to reducing pixel size. Unlike the indirect conversion method, in which an x-ray is temporarily converted to a visible light, with the direct conversion method, an x-ray is directly converted to a charge. Since a high electric field is applied to a photoelectric conversion film, leakage of charge to adjacent pixels can be avoided, so that the pixel size determines the resolution level.

Since a high voltage of a few kV is supplied to the photoelectric conversion film in the direct conversion method, it is necessary to take a countermeasure against the dielectric breakdown of the TFT array.

Figure 6:
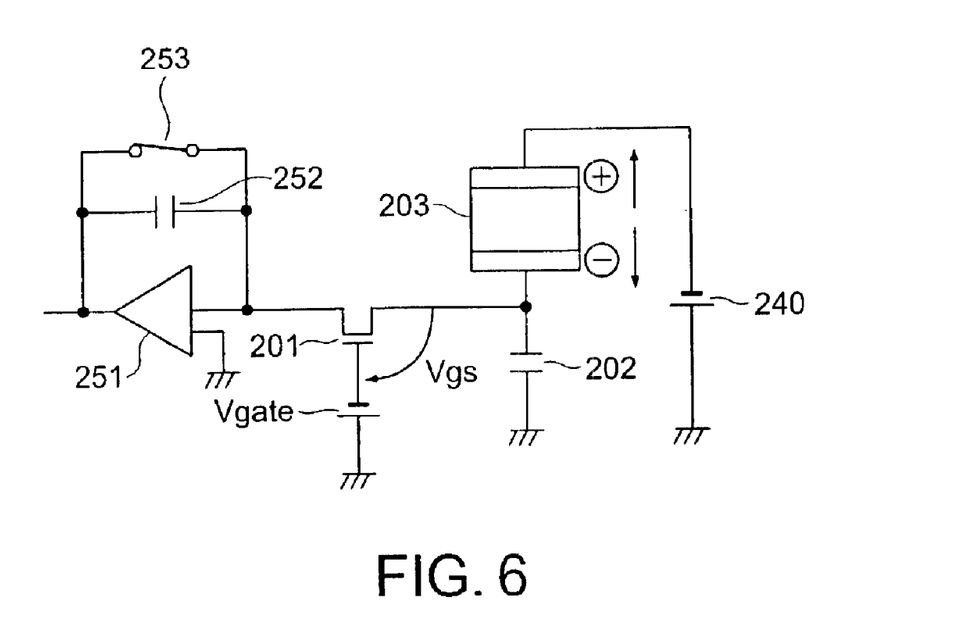
FIG. 6 shows the structure of a conventional imaging device.

Japanese Patent Laid-Open Publication No. 2000-58804 discloses an example of the technique for preventing dielectric breakdown. FIG. 6 shows this technique, in which a negative power supply 240 is connected to one end of a photoelectric conversion film 203, and an accumulative pixel capacitance 202 is connected to the other end thereof. Electrons are accumulated in the accumulative pixel capacitance 202 when an x-ray is received. Further, a source of a TFT 201 is connected to the other end of the photoelectric conversion film 203, and a gate thereof is supplied with a negative voltage. Accordingly, under normal conditions, the gate-source voltage $V_{gs}$ is a negative voltage, and the TFT 201 is in the off state. When an x-ray is received and electrons are accumulated in the accumulative pixel capacitance 202, the gate-source voltage $V_{gs}$ is decreased. When a certain level of signal is received to accumulate electrons sufficiently enough to make the gate-source voltage $V_{gs}$ in the vicinity of zero, the TFT 201 is turned on. Then, a reset switch 253 allows the excessive electrons to be discharged through the signal line and an integral capacitance 252. In this way, voltage applied to the accumulative pixel capacitance 202 is restricted to under a predetermined level, and it is possible to prevent the dielectric breakdown of insulating layer.

Although the dielectric breakdown preventing technique disclosed in Japanese Patent Laid-Open Publication No. 2000-58804 is effective when the x-ray is emitted in a pulse irradiation manner, if the x-ray is emitted in a continuous irradiation manner, noise is increased, resulting in a deterioration of the quality of images. This will be described below.

Figure 7A:
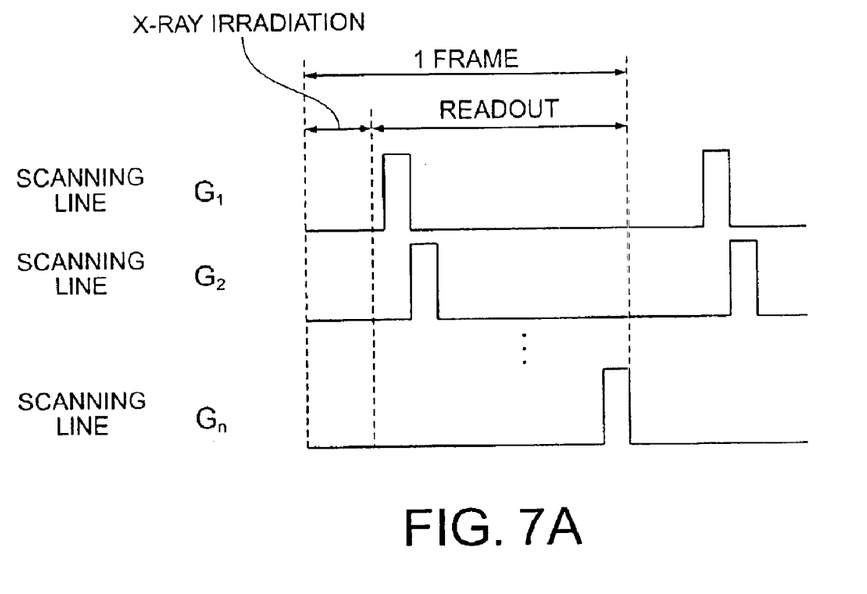
FIG. 7A is a timing chart of the irradiation period and the signal readout period in the case where a pulse irradiation of x-ray is performed.
Figure 7B:
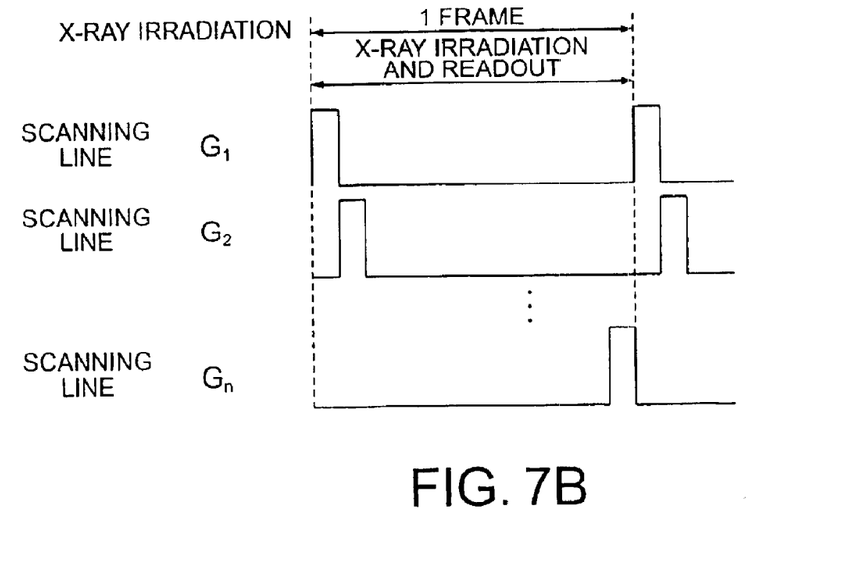
FIG. 7B is a timing chart of the irradiation period and the signal readout period in the case where a continuous irradiation of x-ray is performed.

FIGS. 7A and 7B show the x-ray irradiation period and the signal readout period in the pulse irradiation mode, and the continuous irradiation mode, respectively. FIG. 7A is the timing chart of the pulse irradiation, and FIG. 7B is the timing chart of the continuous irradiation.

In the pulse irradiation mode, the x-ray irradiation period and the signal readout period are temporally separated, as shown in FIG. 7A. In this case, when an excessive dose of x-ray is received, signals beyond the predetermined level (undesired signal) flow through the signal line toward the detection amplifier 251 side. However, since the undesired signal flows only during the x-ray irradiation period, which is temporally different from the signal readout period, the detection amplifier 251 is in the reset state. Accordingly, no undesired signal is detected by the detection amplifier 251.

In the continuous irradiation mode, however, the x-ray irradiation and the signal readout are simultaneously performed, as shown in FIG. 7B. Accordingly, undesired signals are always produced and flow toward the detection amplifier 251. Therefore, the detection amplifier 251 simultaneously detects a pixel signal and an undesired signal, and the undesired signal is recognized as a noise, thereby deteriorating the quality of image.

Figure 10:
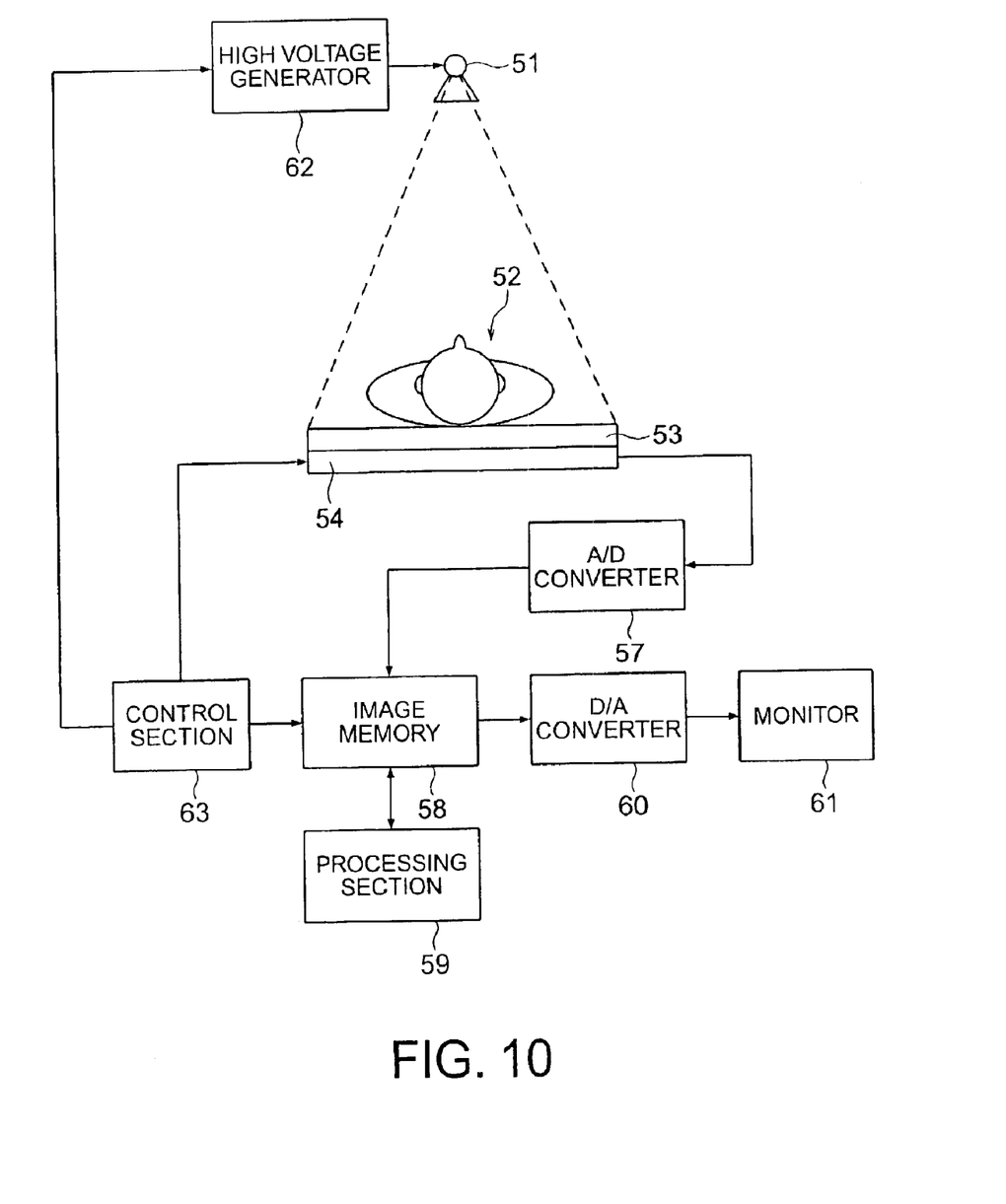
FIG. 10 schematically shows an x-ray imaging device system.

FIG. 10 schematically shows an x-ray imaging device system using TFTs. An x-ray emitted from an x-ray source 51 passes through an object person 52 to reach a TFT imaging device 53, which converts the x-ray to a corresponding analog electric signal. The converted analog signals are converted to digital signals in a time sequential manner by an A/D converter 57, and stored in an image memory 58. The image memory 58 is capable of storing one or more images. A control section 63 transmits a control signal to the image memory 58 so that the image memory 58 sequentially stores data items to predetermined addresses. A processing section 59 retrieves a data item from the image memory 58, processes it, and outputs the result to the image memory 58. The processed data item from the image memory 58 is converted to an analog signal by a D/A converter 60, and displayed on a monitor 61 as an x-ray image. For example, x-ray moving images can be obtained by capturing images at 30 frames per second. However, in such an imaging mode for displaying moving images, if x-rays are continuously emitted to display moving images, noise due to undesired signals is possibly caused as in the case of the x-ray CT system.

SUMMARY OF THE INVENTION

An imaging device according to an aspect of the present invention includes: a plurality of signal lines; a plurality of scanning lines arranged to intersect with the signal lines; pixels each being provided to an intersection of a signal line and a scanning line, and including a photoelectric conversion film converting an x-ray to a charge, a switching element composed of a transistor, of which a gate is connected to a corresponding scanning line, a source is connected to the photoelectric conversion film, and a drain is connected to a corresponding signal line, and a accumulation element connected to the photoelectric conversion film and the switching element, and accumulating the charge produced in the photoelectric conversion element; a scanning line driving circuit driving the scanning lines; and a signal detection circuit connected to the signal lines and reading out the charge accumulated in the accumulation element, a potential of the photoelectric conversion film and a gate potential of the switching element being set such that an absolute value of a gate-source voltage of the switching element decreases when the charge is accumulated in the accumulation element, and the scanning line driving circuit outputting at least two kinds of scanning line voltages that can turn off the switching element.

BRIEF DESCRIPTION OF THE DRAWINGS

FIGS. 2(*a*) to 2(*c*) are timing charts of scanning line driving signals of the first embodiment, in which FIG. 2(*a*) represents a signal for driving the scanning line $G_j$, FIG. 2(*b*) represents a signal for driving the scanning line $G_{j+1}$, and FIG. 2(*c*) represents a signal for driving the scanning line $G_{j+2}$.

FIGS. 12(*a*) to 12(*c*) are timing charts of scanning line driving signals of the third embodiment, in which FIG. 12(*a*) represents a signal for driving the scanning line $G_j$, FIG. 12(*b*) represents a signal for driving the scanning line $G_{j+1}$, and FIG. 12(*c*) represents a signal for driving the scanning line $G_{j+2}$.

DESCRIPTION OF THE EMBODIMENTS

Hereinafter, embodiments of the present invention will be described with reference to the accompanying drawings.
(First Embodiment)

Figure 1:
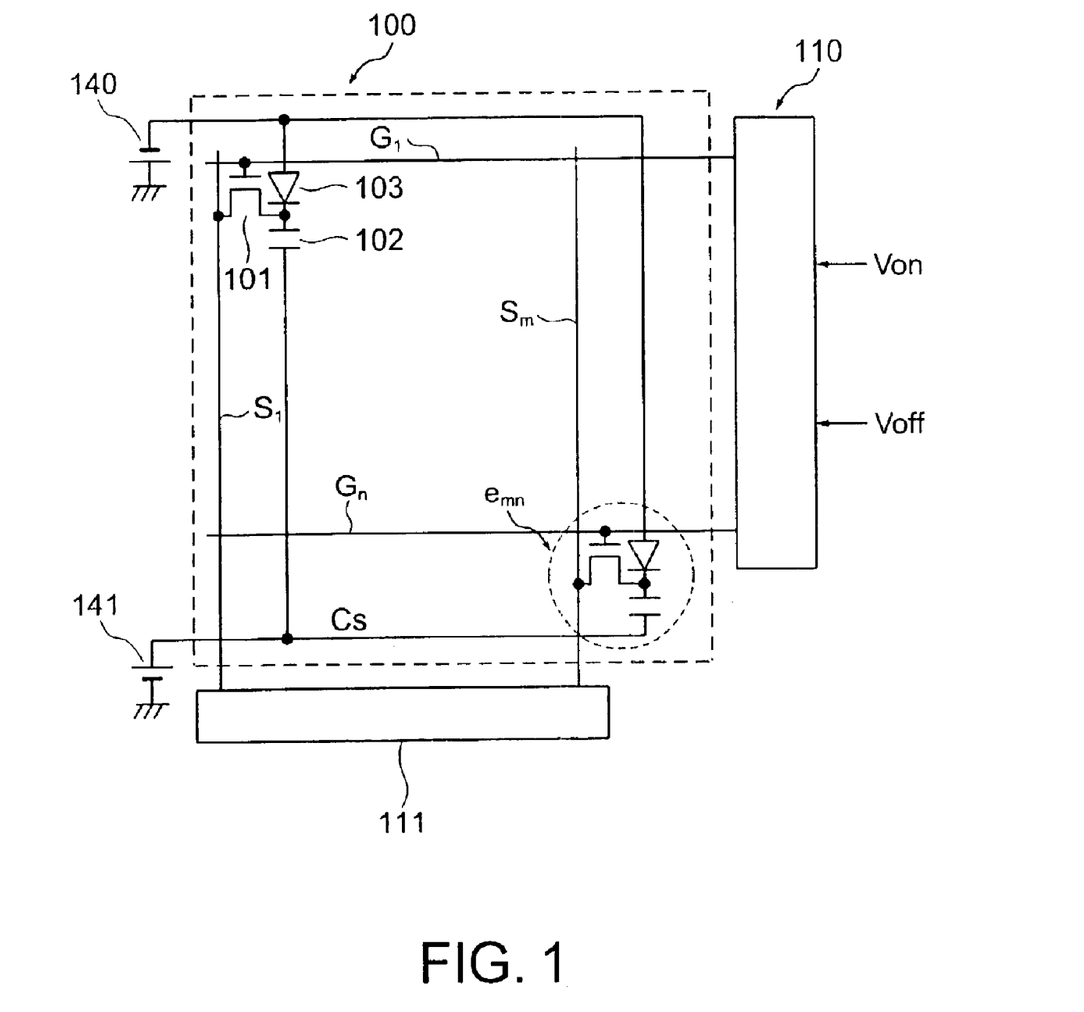
FIG. 1 is a block diagram showing the structure of an imaging device according to the first embodiment of the present invention.

FIG. 1 shows the structure of an imaging device according to the first embodiment of the present invention. The imaging device includes a TFT array 100, a scanning line driving circuit 110, and a detection amplifier circuit 111. The TFT array 100 includes m of signal lines $S_1, \ldots, S_m$, n of scanning lines $G_1, \ldots, G_n$, m×n of pixels $e_{ij}$ (i=1, ..., m, and j=1, ..., n) arranged in a matrix form, and a capacitive wiring $C_s$. Each scanning line $G_j$ (j=1, ..., n) is connected to the scanning line driving circuit 110, and each signal line $S_i$ (i=1, ..., m) is arranged so as to be orthogonal to the n of scanning lines $G_1 \ldots, G_n$, and connected to the detection amplifier circuit 111.

Each pixel $e_{ij}$ (i=1, ..., m, and j=1, ..., n) is located at an intersection of a signal line $S_i$ and a scanning line $G_j$, and has a switching element 101 formed of a TFT (Thin Film Transistor), a pixel accumulative capacitance 102, and a photoelectric conversion film 103. The gate of the switching element 101 is connected to the corresponding scanning line $G_j$; the drain is connected to the corresponding signal line $S_i$; and the source is connected to one end of the pixel accumulative capacitance 102. The other end of the pixel accumulative capacitance 102 is connected to a power supply 141 via the capacitive wiring $C_s$. One end of the photoelectric conversion film 103 is connected to the source of the switching element 101; and the other end is connected to a negative power supply 140.

In this embodiment, a gate-on voltage $V_{on}$ and a gate-off voltage $V_{off}$ are externally applied to the scanning line driving circuit 110. The gate-off voltage $V_{off}$ has two levels of potentials $V_{off1}$ and $V_{off2}$, which are applied to the scanning line $G_j$ (j=1, ..., n) selected by the scanning line driving circuit 110.

Next, the operation of the imaging device according to this embodiment will be explained with reference to FIGS. 2 and 3.

Figure 2:
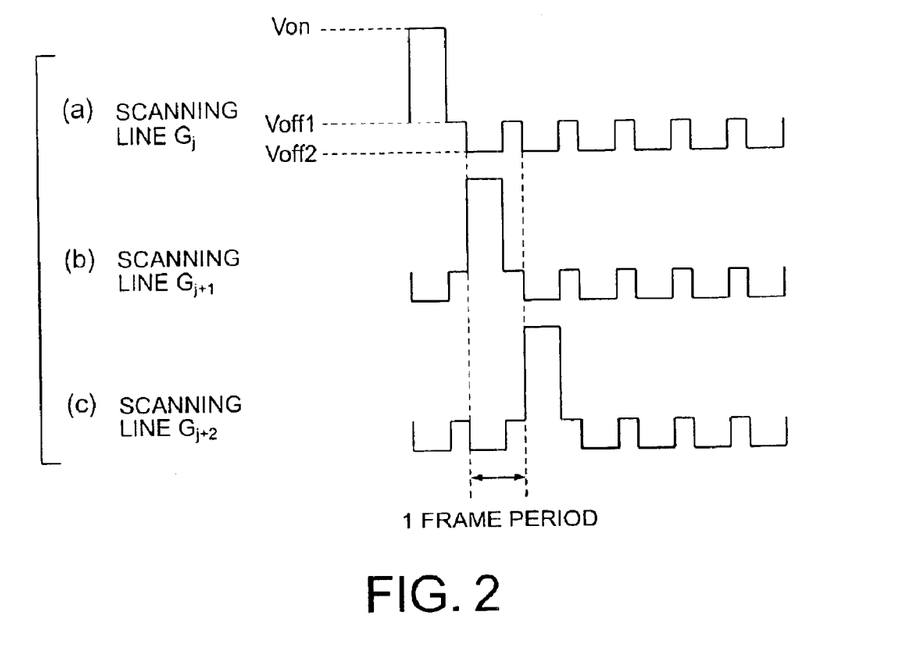

FIGS. 2(*a*) to 2(*c*) are timing charts representing the scanning line potentials of the scanning lines $G_j$, $G_{j+1}$, and $G_{j+2}$. When the photoelectric conversion film 103 receives an x-ray, electron-hole pairs corresponding to the x-ray dose are generated, so that electrons are accumulated in the pixel accumulative capacitance 102. The x-ray is always emitted.

In FIGS. 2(a) to 2(c), the scanning line potential of the scanning line $G_j$ (j=1, ..., n) is set to be at the gate-on voltage $V_{on}$ during the period of the signal of the pixel connected to the scanning line $G_j$ is read, and set to be at the gate-off voltage $V_{off}$ ($V_{off1}$, $V_{off2}$) during the other periods. The scanning line from which the signal is read is sequentially selected, such as in the order of $G_j$, $G_{j+1}$, $G_{j+2}$, ..., and the gate-on voltage $V_{on}$ is sequentially applied to the selected scanning lines. In the periods other than the signal readout period, the gate-off voltage $V_{off}$ ($V_{off1}$, $V_{off2}$) is applied to the scanning line $G_j$. A period during which the potential of the scanning line $G_j$ is set to be at the gate-off voltage $V_{off2}$ matches the period during which the potential of at least one of the scanning lines $G_k$ (k≠j) other than the scanning line $G_j$ is set to be at the gate-on voltage $V_{on}$. The gate-off voltage $V_{off1}$ is applied to the scanning line $G_j$ during the periods other than the above-described signal readout period and the periods during which the gate-off voltage $V_{off2}$ is applied. A period during which the potential of the scanning line $G_j$ becomes the gate-off voltage $V_{off2}$ can be set so as to match the period during which the potential of at least one of the other scanning lines $G_k$ (k≠j) becomes the gate-on voltage $V_{on}$.

Figure 3:
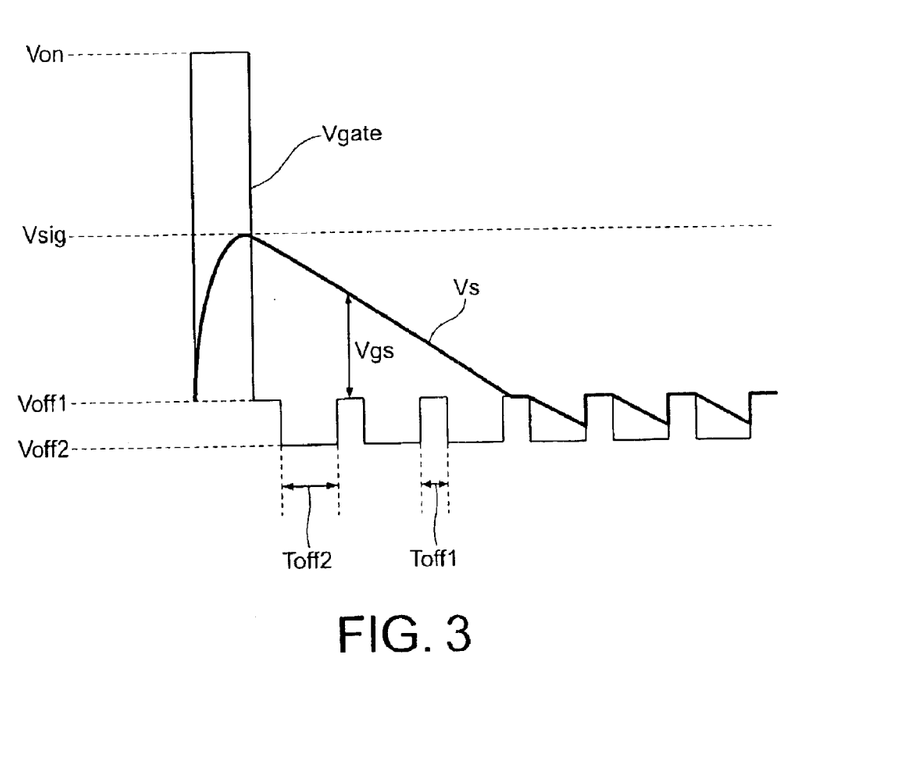
FIG. 3 is a timing chart of a scanning line driving signal and a pixel potential of the first embodiment.

FIG. 3 shows the waveforms of the scanning line potential $V_{gate}$ of a certain scanning line $G_j$ (j=1, ..., n) and the pixel potential of a pixel $e_{ij}$ (i=1, ..., m) connected to the scanning line $G_j$, i.e., the source potential $V_s$ of the switching element 101. The pixel potential $V_s$ of the pixel $e_{ij}$ is read out during the period the gate of the switching element 101 of this pixel is in the on state, i.e., the gate-on voltage $V_{on}$ is applied to the gate of the switching element 101. The pixel potential $V_s$ becomes substantially the same as the signal line potential $V_{sig}$ immediately before the scanning line potential $V_{gate}$ changes from the gate-on voltage $V_{on}$ to the gate-off voltage $V_{off1}$. Signals are accumulated in the pixel accumulative capacitance 102 during the period the switching element 101 is in the off state, i.e., the gate-off voltage $V_{off}$ is applied to the gate of the switching element 101. Accordingly, the pixel potential $V_s$ changes in such a direction that the absolute value $|V_{gs}|$ of the gate-source potential $V_{gs}$ of the switching element 101 decreases. Since the switching element 101 is of n-type, in FIG. 3, the signals are accumulated so that the pixel potential $V_s$ moves in the negative direction relative to the signal line potential $V_{sig}$.

When the absolute value $|V_{gs}|$ of the gate-source potential becomes substantially zero, excessive signals are discharged to the corresponding signal lines as undesired signals. At this time, the level of the pixel potential $V_s$, at which the absolute value $|V_{gs}|$ is zero, can be further changed by setting two levels of gate-off voltages $V_{off1}$ and $V_{off2}$. Accordingly, it is possible to adjust the accumulative level of signals. Specifically, during the period $T_{off1}$, in which the gate-off voltage is $V_{off1}$, the absolute value $|V_{gs}|$ is zero, and signals are sufficiently accumulated to turn on the switching element 101 (so as to discharge undesired signals). However, during the period $T_{off2}$, in which the gate-off voltage is $V_{off2}$, the gate potential $V_g$ changes in the direction to make the absolute value $|V_{gs}|$ increase, the switching element 101 is turned off, which enables further accumulation of signals. Since no undesired signal flows through the signal line in the period $T_{off2}$, in which the gate-off voltage is $V_{off2}$, it is possible to detect only a pixel signal.

As described above, according to the imaging device of this embodiment, it is possible to temporally separate the signal readout period from the undesired signal discharge period even in the x-ray continuous irradiation mode, by supplying two levels of potentials for turning off the switching element. Thus, it is not necessary to simultaneously read out the pixel signal and the undesired signal, making it possible to obtain a good image with less noise (undesired signals).

(Second Embodiment)

Figure 4:
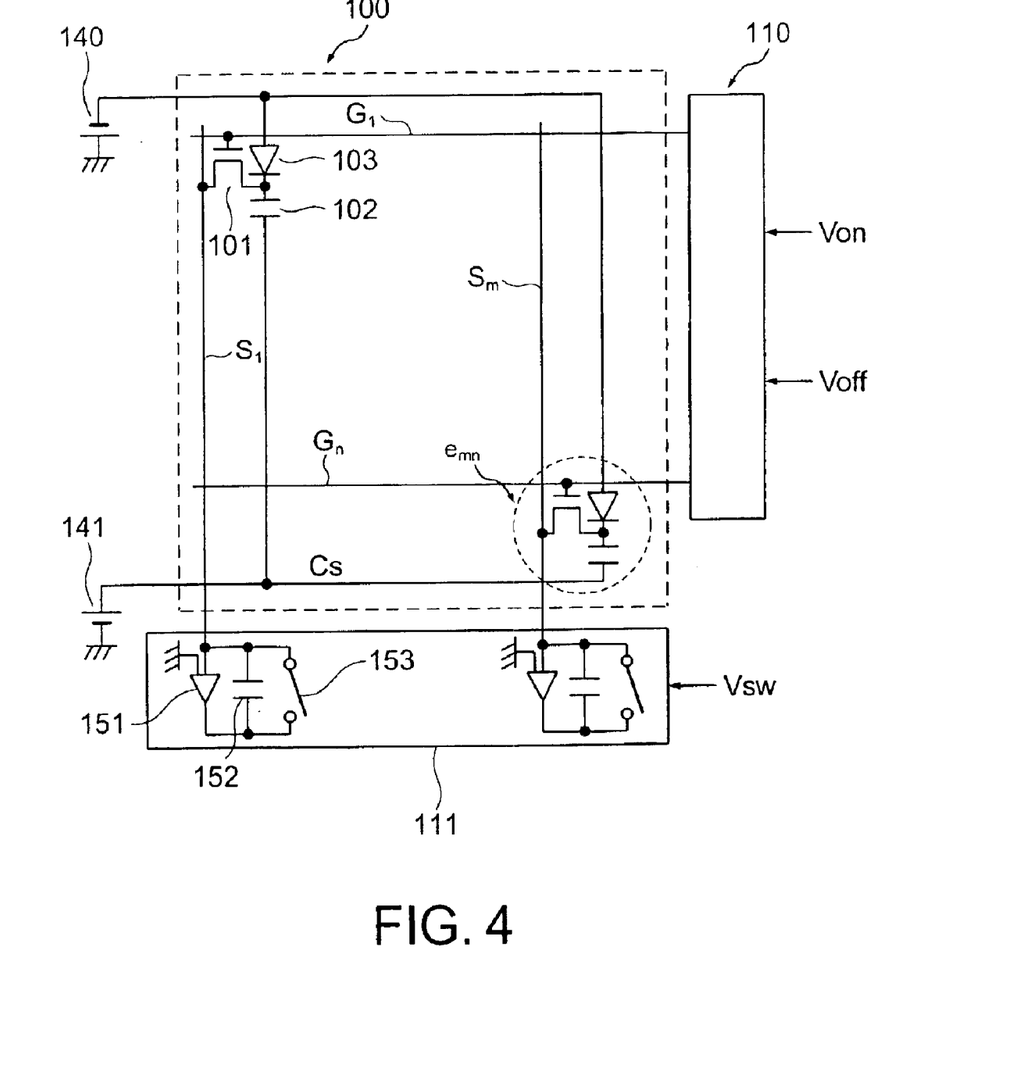
FIG. 4 is a block diagram showing the structure of an imaging device according to the second embodiment of the present invention.

FIG. 4 shows the structure of an imaging device according to the second embodiment of the present invention, which is obtained by specifying in more detail the detection amplifier 111 of the first embodiment shown in FIG. 1. The detection amplifier circuit 111 of this embodiment includes an integration amplifier 151, an integral capacitance 152, and a reset switch 153 for each signal line $S_i$ (i=1, ..., m). The integral capacitance 152 and the reset switch 153 are connected in parallel with the integration amplifier 151. The on state and the off state of the reset switch 153 are controlled by a control signal $V_{sw}$, which is externally inputted.

Figure 5:
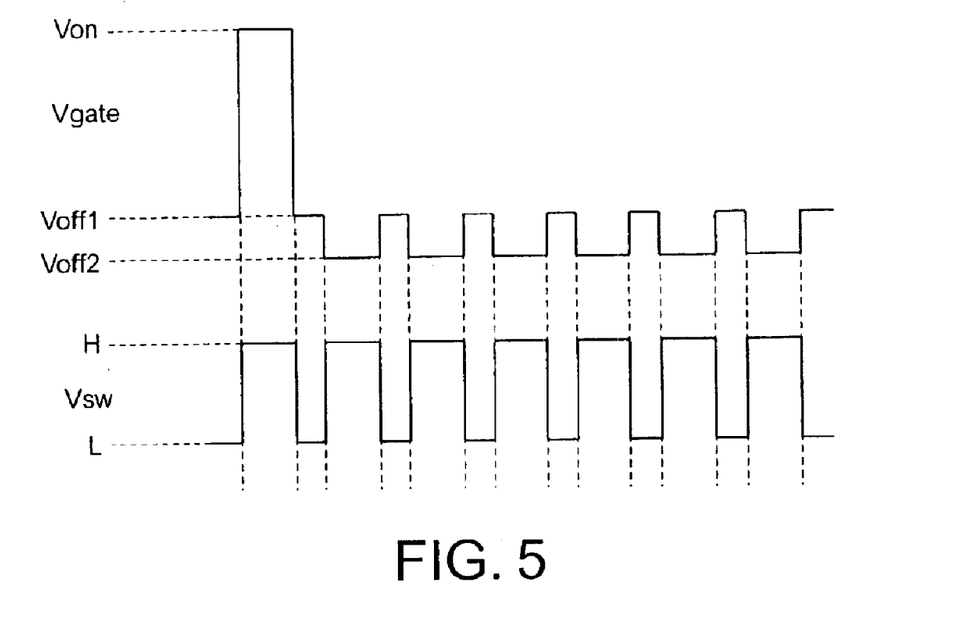
FIG. 5 is a timing chart of a scanning line driving signal and a reset signal of the detection amplifier in the second embodiment.

The operation of the second embodiment will be described with reference to FIG. 5, which is a timing chart of the potential $V_{gate}$ of the scanning line $G_j$ (j=1, ..., n) and the control signal $V_{sw}$ for controlling the reset switch 153. In FIG. 5, the reset switch 153 is in the off state when the control signal $V_{sw}$ is at the "H" level, and in the on state when the control signal $V_{sw}$ is at the "L" level.

In this embodiment, the periods during which the control signal $V_{sw}$ is at the "H" level do not match the periods during which the scanning line potential $V_{gate}$ is at $V_{off1}$, and the periods during which the scanning line potential $V_{gate}$ is at $V_{off1}$ match the periods during which the control signal $V_{sw}$ is at the "L" level. In this manner, it is possible to eliminate the influence of noise caused by the parasitic capacitance. Although the periods during which the scanning line potential $V_{gate}$ is at $V_{off1}$ match the periods during which the control signal $V_{sw}$ is at the "L" level in the above explanation, it is possible that the periods during which the control signal $V_{sw}$ is at the "L" level include the periods during which the scanning line potential $V_{gate}$ is at $V_{off1}$.

With the waveforms shown in FIG. 5, the undesired signals flowing through the signal line are not accumulated in the integration capacitance 152, which enables the detection amplifier 151 to detect only pixel signals.

Accordingly, it is possible to obtain good images with less noise by detecting signals in accordance with the waveforms shown in FIG. 5.

The imaging device of the first or second embodiment can be used as a detector of an x-ray CT device. That is, the x-ray CT device includes an x-ray source for emitting x-rays, and an imaging device according to the first or second embodiment for receiving the x-rays emitted from the x-ray source via an object person.

Furthermore, the imaging device according to the first or second embodiment can be used as a detector of an x-ray imaging device.

(Third Embodiment)

Figure 11:
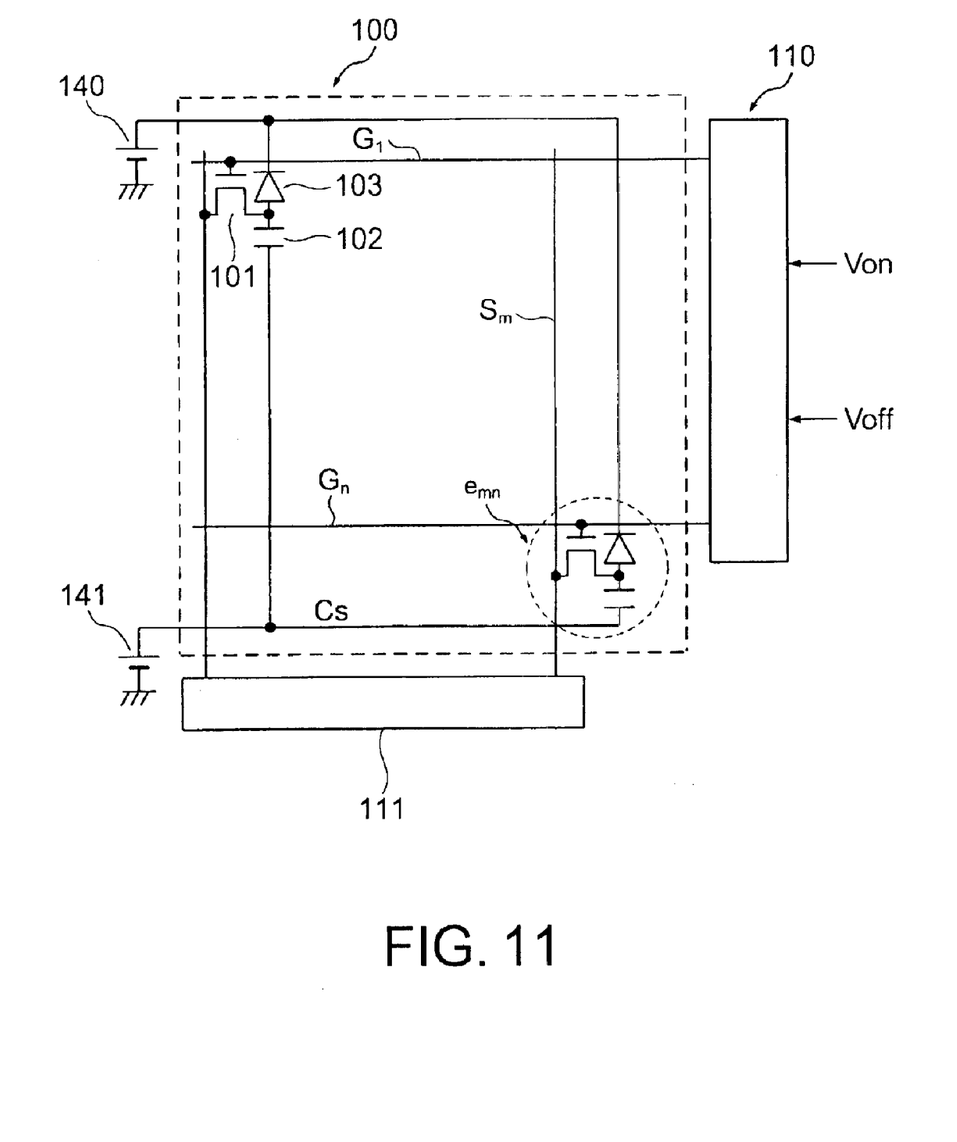
FIG. 11 is a block diagram showing the structure of an imaging device according to the third embodiment of the present invention.

FIG. 11 shows the structure of an imaging device according to the third embodiment of the present invention. In this embodiment, a switching element 101 is of p-type, and holes are accumulated in a pixel accumulative capacitance 102. The basic structure of the third embodiment is the same as that of the first embodiment, and hence the corresponding elements are assigned the same reference numerals as those in the first embodiment, and the detailed explanations thereof are omitted.

In FIG. 11, the switching element 101 is a p-type TFT. A power supply 140 applied a positive voltage to a photoelectric conversion film 103. Holes are accumulated in the pixel accumulative capacitance 102, and outputted to a detection amplifier at the same time as the gate-on voltage $V_{on}$ of a scanning line driving circuit 110.

Figure 12:
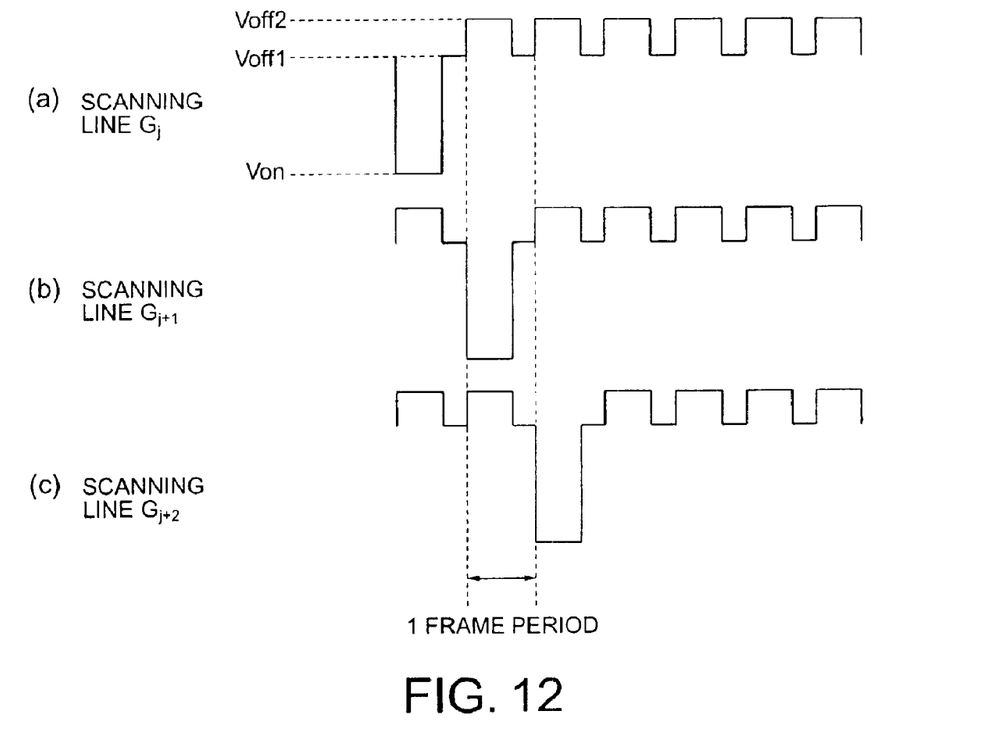

Next, the operation of the imaging device according to this embodiment will be described with reference to FIGS. 12(a) to 13. FIGS. 12(a), 12(b), and 12(c) are timing charts each representing the scanning potential of the scanning line $G_j$, $G_{j+1}$, or $G_{j+2}$.

In FIGS. 12(a) to 12(c), the scanning line potential of the scanning line $G_j$ (j=1, ..., n) is set to be at the gate-on voltage $V_{on}$ during the period of the signal of the pixel connected to the scanning line $G_j$ is read, and set to be at the gate-off voltage $V_{off}$ ($V_{off1}$, $V_{off2}$) during the other periods. The scanning line from which the signal is read is sequentially selected, such as in the order of $G_j$, $G_{j+1}$, $G_{j+2}$, ..., and the gate-on voltage $V_{on}$ is sequentially applied to the selected scanning lines. In the periods other than the signal readout period, the gate-off voltage $V_{off}$ ($V_{off1}$, $V_{off2}$) is applied to the scanning line $G_j$. A period during which the potential of the scanning line $G_j$ is set to be at the gate-off voltage $V_{off2}$ matches the period during which the potential of at least one of the scanning lines $G_k$ (k≠j) other than the scanning line $G_j$ is set to beat the gate-on voltage $V_{on}$. The gate-off voltage $V_{off1}$ is applied to the scanning line $G_j$ during the periods other than the above-described signal readout period and the periods during which the gate-off voltage $V_{off2}$ is applied. A period during which the potential of the scanning line $G_j$ becomes the gate-off voltage $V_{off2}$ can be set so as to match the period during which the potential of at least one of the other scanning lines $G_k$ (k≠j) becomes the gate-on voltage $V_{on}$.

Figure 13:
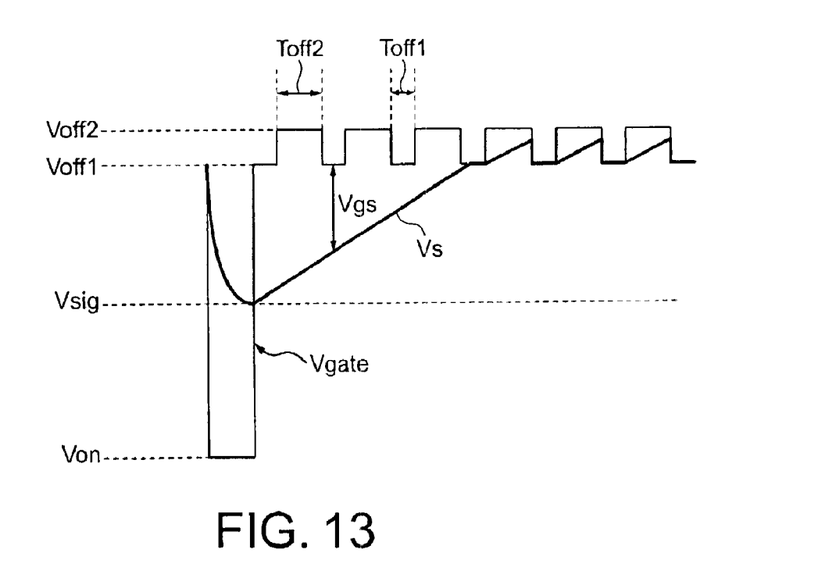
FIG. 13 is a timing chart of a scanning line driving signal and a pixel potential of the third embodiment.

FIG. 13 shows the waveforms of the scanning line potential $V_{gate}$ of a certain scanning line $G_j$ (j=1, ..., n) and the pixel potential of a pixel $e_{ij}$ (i=1, ..., m) connected to the scanning line $G_j$, i.e., the source potential $V_s$ of the switching element 101. The pixel potential $V_s$ of the pixel $e_{ij}$ is read out during the period the gate of the switching element 101 of this pixel is in the on state, i.e., the gate-on voltage $V_{on}$ is applied to the gate of the switching element 101. The pixel potential $V_s$ becomes substantially the same as the signal line potential $V_{sig}$ immediately before the scanning line potential $V_{gate}$ changes from the gate-on voltage $V_{on}$ to the gate-off voltage $V_{off1}$. Signals are accumulated in the pixel accumulative capacitance 102 during the period the switching element 101 is in the off state, i.e., the gate-off voltage $V_{off}$ is applied to the gate of the switching element 101. Accordingly, the pixel potential $V_s$ changes in such a direction that the absolute value $|V_{gs}|$ of the gate-source potential $V_{gs}$ of the switching element 101 decreases. Since the switching element 101 is of p-type in FIG. 13, the signals are accumulated so that the pixel potential $V_s$ moves in the positive direction relative to the signal line potential $V_{sig}$.

When the absolute value $|V_{gs}|$ of the gate-source potential becomes substantially zero, excessive signals are discharged to the corresponding signal lines as undesired signals. At this time, the level of the pixel potential $V_s$, at which the absolute value $|V_{gs}|$ is zero, can be further changed by setting two levels of gate-off voltages $V_{off1}$ and $V_{off2}$. Accordingly, it is possible to adjust the accumulative level of signals. Specifically, during the period $T_{off1}$, in which the gate-off voltage is $V_{off2}$, the absolute value $|V_{gs}|$ is zero, and signals are sufficiently accumulated to turn on the switching element 101 (so as to discharge undesired signals). However, during the period $T_{off2}$, in which the gate-off voltage is $V_{off2}$, the gate potential $V_g$ changes in the direction to make the absolute value $|V_{gs}|$ increase, the switching element 101 is turned off, which enables further accumulation of signals. Since no undesired signal flows through the signal line in the period $T_{off2}$, in which the gate-off voltage is $V_{off2}$, it is possible to detect only a pixel signal.

As described above, according to the imaging device of this embodiment, it is possible to temporally separate the signal readout period from the undesired signal discharge period even in the x-ray continuous irradiation mode, by supplying two levels of potentials for turning off the switching element. Thus, it is not necessary to simultaneously read out the pixel signal and the undesired signal, making it possible to obtain a good image with less noise (undesired signals).

(Fourth Embodiment)

Figure 14:
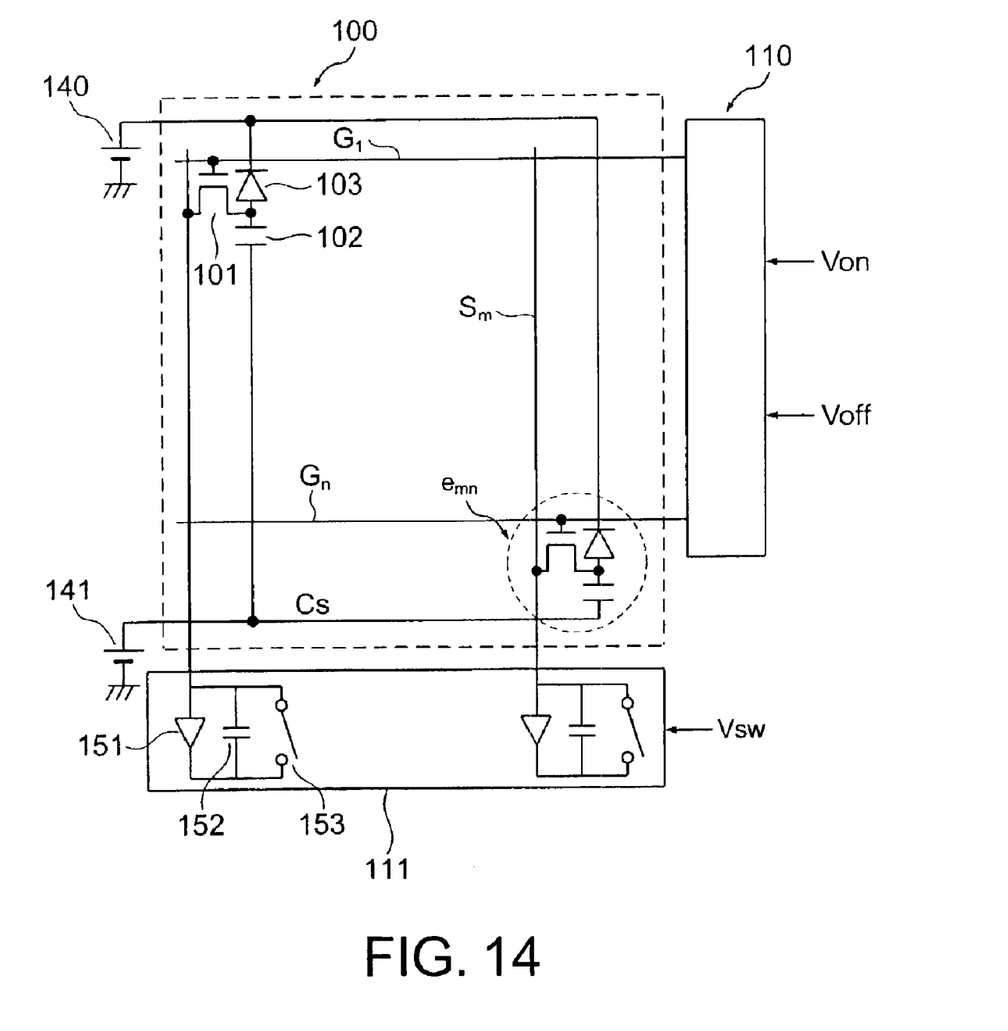
FIG. 14 is a block diagram showing the structure of an imaging device according to the fourth embodiment of the present invention.

FIG. 14 shows the structure of an imaging device according to the fourth embodiment of the present invention, which is obtained by specifying in more detail the detection amplifier 111 of the third embodiment shown in FIG. 11. The detection amplifier circuit 111 of this embodiment includes an integration amplifier 151, an integral capacitance 152, and a reset switch 153 for each signal line $S_i$ (i=1, ..., m). The integral capacitance 152 and the reset switch 153 are connected in parallel with the integration amplifier 151. The on state and the off state of the reset switch 153 are controlled by a control signal $V_{sw}$, which is externally inputted.

Figure 15:
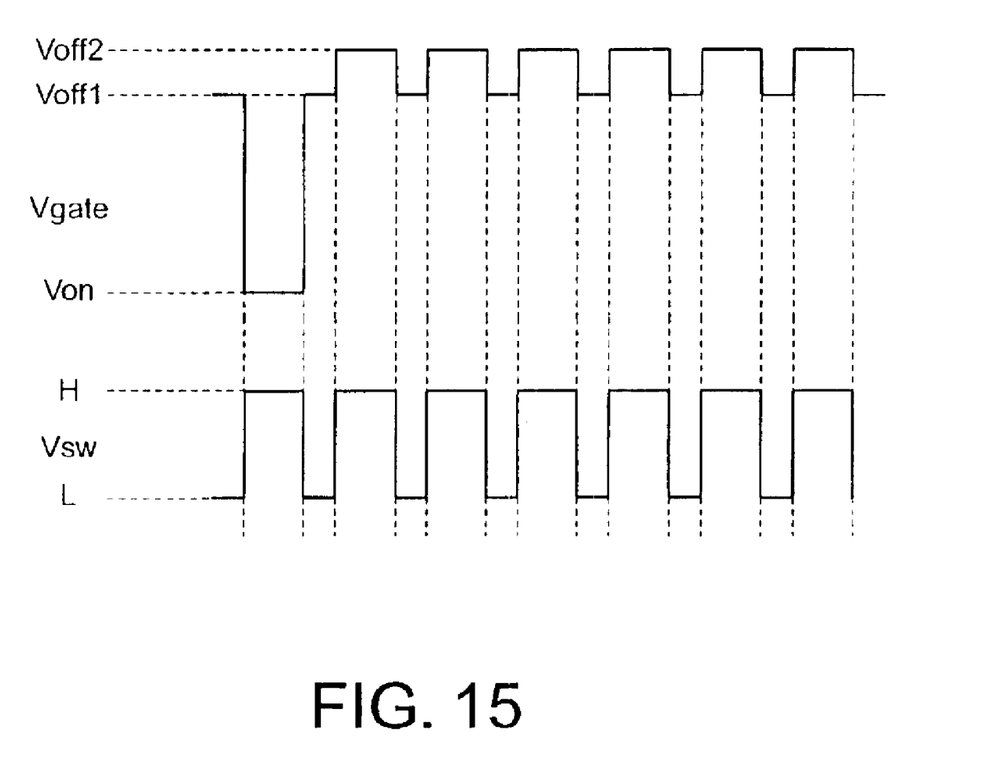
FIG. 15 is a timing chart of a scanning line driving signal and a reset signal of the detection amplifier in the fourth embodiment.

The operation of the fourth embodiment will be described with reference to FIG. 15, which is a timing chart of the potential $V_{gate}$ of the scanning line $G_j$ (j=1, ..., n) and the control signal $V_{sw}$ for controlling the reset switch 153. In FIG. 15, the reset switch 153 is in the off state when the control signal $V_{sw}$ is at the "H" level, and in the on state when the control signal $V_{sw}$ is at the "L" level.

In this embodiment, the periods during which the control signal $V_{sw}$ is at the "H" level do not match the periods during which the scanning line potential $V_{gate}$ is at $V_{off1}$, and the periods during which the scanning line potential $V_{gate}$ is at Voff1 match the periods during which the control signal $V_{sw}$ is at the "L" level. In this manner, it is possible to eliminate the influence of noise Caused by the parasitic capacitance. Although the periods during which the scanning line potential $V_{gate}$ is at $V_{off1}$ match the periods during which the control signal $V_{sw}$ is at the "L" level in the above explanation, it is possible that the periods during which the control signal $V_{sw}$ is at the "L" level include the periods during which the scanning line potential $V_{gate}$ is at $V_{off1}$.

With the waveforms shown in FIG. 15, the undesired signals flowing through the signal line are not accumulated in the integration capacitance 152, which enables the detection amplifier 151 to detect only pixel signals.

Accordingly, it is possible to obtain good images with less noise by detecting signals in accordance with the waveforms shown in FIG. 15.

The imaging device of the third or fourth embodiment can be used as a detector of an x-ray CT system. That is, the x-ray CT system includes an x-ray source for emitting x-rays, and an imaging device according to the third or fourth embodiment for receiving the x-rays emitted from the x-ray source via an object person.

Furthermore, the imaging device according to the third or fourth embodiment can be used as a detector of an x-ray imaging device system.

As described above, according to the present invention, even in the x-ray continuous irradiation mode, it is possible to obtain good images.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concepts as defined by the appended claims and their equivalents.

What is claimed is:

1. An imaging device comprising:
   a plurality of signal lines;
   a plurality of scanning lines arranged to intersect with the signal lines;
   pixels each being provided to an intersection of a signal line and a scanning line, and including a photoelectric conversion film converting an x-ray to a charge, a switching element composed of a transistor, of which a gate is connected to a corresponding scanning line, a source is connected to the photoelectric conversion film, and a drain is connected to a corresponding signal line, and a accumulation element connected to the photoelectric conversion film and the switching element, and accumulating the charge produced in the photoelectric conversion element;
   a scanning line driving circuit driving the scanning lines; and
   a signal detection circuit connected to the signal lines and reading out the charge accumulated in the accumulation element,
   a potential of the photoelectric conversion film and a gate potential of the switching element being set such that an absolute value of a gate-source voltage of the switching element decreases when the charge is accumulated in the accumulation element, and
   the scanning line driving circuit outputting at least two kinds of scanning line voltages that turn off the switching element.

2. The imaging device according to claim 1, wherein when a scanning line voltage that keeps the switching element in an on state is applied to one scanning line, all of the other scanning lines are supplied with a scanning line voltage that makes the absolute value of the gate-source voltage of the switching element increase, which is selected from the at least two kinds of scanning line voltages that turn off the switching element.

3. The imaging device according to claim 2, wherein a first period does not match a second period, the first period being a period during which a scanning line voltage making the absolute value of the gate-source voltage decrease is selected from the at least two kinds of scanning line voltages, and the second period being a period during which a signal is detected by the signal detection circuit.

4. The imaging device according to claim 2, wherein
   the signal detection circuit includes an integration amplifier, an integration capacitance connected in parallel with the integration amplifier, and a reset switch connected in parallel with the integration amplifier and controlled to be turned on or off by a control signal, and
   the reset switch is kept to be in an on state by the control signal during a period the scanning line voltage that makes the absolute value of the gate-source voltage decrease is selected from the at least two kinds of scanning line voltages that turn off the switching element.

5. The imaging device according to claim 2, wherein
   the switching element is an n-type thin film transistor,
   one end of the photoelectric conversion film is connected to the source of the switching element and the other end of the photoelectric conversion film is connected to a negative power supply, and
   one end of the accumulation element is connected to the source of the switching element.

6. The imaging device according to claim 2, wherein
   the switching element is a p-type thin film transistor,
   one end of the photoelectric conversion film is connected to the source of the switching element and the other end of the photoelectric conversion film is connected to a positive power supply, and
   one end of the accumulation element is connected to the source of the switching element.

7. The imaging device according to claim 1, wherein a first period does not match a second period, the first period being a period during which a scanning line voltage making the absolute value of the gate-source voltage decrease is selected from the at least two kinds of scanning line voltages, and the second period being a period during which a signal is detected by the signal detection circuit.

8. The imaging device according to claim 1, wherein
   the signal detection circuit includes an integration amplifier, an integration capacitance connected in parallel with the integration amplifier, and a reset switch connected in parallel with the integration amplifier and controlled to be turned on or off by a control signal, and
   the reset switch is kept to be in an on state by the control signal during a period the scanning line voltage that makes the absolute value of the gate-source voltage decrease is selected from the at least two kinds of scanning line voltages that turn off the switching element.

9. An x-ray computerized tomography system comprising:
   an x-ray source emitting an x-ray; and
   the imaging device according to claim 8, receiving the x-ray from the x-ray source.

10. An x-ray imaging device system comprising:
    an x-ray source emitting an x-ray; and
    the imaging device according to claim 8, receiving the x-ray from the x-ray source.

11. The imaging device according to claim 1, wherein
    the switching element is an n-type thin film transistor,
    one end of the photoelectric conversion film is connected to the source of the switching element and the other end of the photoelectric conversion film is connected to a negative power supply, and
    one end of the accumulation element is connected to the source of the switching element.

12. The imaging device according to claim 1, wherein
    the switching element is a p-type thin film transistor,
    one end of the photoelectric conversion film is connected to the source of the switching element and the other end of the photoelectric conversion film is connected to a positive power supply, and
    one end of the accumulation element is connected to the source of the switching element.

13. An x-ray computerized tomography system comprising:
    an x-ray source emitting an x-ray; and
    the imaging device according to claim 1, receiving the x-ray from the x-ray source.

14. An x-ray imaging device system comprising:
    an x-ray source emitting an x-ray; and
    the imaging device according to claim 1, receiving the x-ray from the x-ray source.

* * * * *